United States Patent [19]
Schwartz et al.

[11] Patent Number: 5,610,173
[45] Date of Patent: Mar. 11, 1997

[54] FORMULATIONS FOR LIPOPHILIC COMPOUNDS

[75] Inventors: Donna P. Schwartz, San Mateo; Laura K. Shawver, San Francisco, both of Calif.

[73] Assignee: Sugen, Inc., Redwood City, Calif.

[21] Appl. No.: 429,206

[22] Filed: Apr. 26, 1995

Related U.S. Application Data

[63] Continuation-in-part of Ser. No. 370,574, Jan. 6, 1995, which is a continuation-in-part of Ser. No. 179,570, Jan. 7, 1994.

[51] Int. Cl.$^6$ .......................... A61K 31/42; A61K 31/165
[52] U.S. Cl. ............................................. 514/378; 514/626
[58] Field of Search ..................... 514/378, 626

[56] References Cited

U.S. PATENT DOCUMENTS

| | | | |
|---|---|---|---|
| 4,087,535 | 5/1978 | Heubach et al. | 424/272 |
| 4,284,786 | 8/1981 | Kammerer et al. | 548/248 |
| 4,351,841 | 9/1982 | Kammerer et al. | 424/272 |
| 4,992,271 | 2/1991 | Fernandez et al. | 424/85.2 |
| 5,268,382 | 12/1993 | Bartlett et al. | 514/378 |
| 5,314,685 | 5/1994 | Tyle et al. | 424/401 |
| 5,403,858 | 4/1995 | Bastard et al. | 514/449 |

FOREIGN PATENT DOCUMENTS

| | | |
|---|---|---|
| 0359184 | 9/1989 | European Pat. Off. . |
| 0413329 | 2/1991 | European Pat. Off. . |
| 0522937 | 7/1992 | European Pat. Off. . |
| 0551230 | 7/1993 | European Pat. Off. . |
| 0607777 | 7/1994 | European Pat. Off. . |
| 0607775 | 7/1994 | European Pat. Off. . |
| 0607776 | 7/1994 | European Pat. Off. . |
| 0645145 | 9/1994 | European Pat. Off. . |
| 9117748 | 11/1991 | WIPO . |

OTHER PUBLICATIONS

Satou Fumihiro, "Injection Containing Etoposide," Application No. JP60239415 published Nov. 28, 1985, Application No. JP84009559 dated May 15, 1984, *Patent Abstract of Japan* vol.105, No. 112 (C–342).
Andrews et al. (American Veterinary Medicine Association Panel on Euthanasia), "1993 Report of the AVMA Panel on Authanasia", *J. American Veterinary Medicine Association* 202(2):229–249 (1993).
Bartlett et al., "Effects of leflunomide on immune responses and models of inflammation," *Springer Semin. Immunopathol.* 14:381–394 (1993).
Bartlett et al., "Leflunomide (HWA 486), a novel immunomodulating compound for the treatment of autoimmune disorders and reactions leading to transplantation rejection," *Agents and Actions* 32:10–21 (1991).
Bartlett et al., "Leflunomide: A novel immunomodulating drug" in *Nonsteroidal Anti–Inflammatory Drugs* 2nd ed. pp. 349–366, Lewis and Furstk eds., Dekker, NY NY, 1991.
*Cecil Textbook of Medicine*, eds. Wyngaarden, Smith, Bennett, W.B. Saunders (1992) p. 2220.

Cherwinski et al., "The Immunosuppressant Leflunomide Inhibits Lymphocyte Progression Through Cell Cycle by a Novel Mechanism," *J. Pharmacology and Exp. Therap.* 272:460–468 (1995).
Chong et al., "Leflunomide, a Novel Immunomodulatory Agent: In Vitro Analyses of the Mechanism of Immunosupression," *Transplant. Proc.* 25:747–749 (1993).
Chong et al., "Leflunomide, a Novel Immunosuppressive Agent," *Transplantation* 55:1361–1366 (1993).
Glant et al., "Immunodulation of proteoglycan–induced progessive polyarthritis by leflunomide," *Immunopharmacology* 23:105–116 (1992).
Hambelton and Mahon, "Drug actions on delayed–type hypersensitivity in rats with developing and established adjuvant arthritis," *Agents and Actions* 29:328–332 (1990).
Ju et al., "Leflunomide inhibits cytokine–induced DNA synthesis of rabbit synovial cells in culture," *Zhongguo Yaoli Xuebao* 15:223–226 (1994).
Ju et al., "Leflunomide inhibits PAF induced DNA synthesis in rabbit synovial cells and PAF production from rat peritomeal macrophages," *Yaoxue Xuebao* 92:90–94 (1994).
Kuechle et al., "Prevention of Kidney and Skin Graft Rejection in Rats by Leflunomide, a New Immunodulating Agent," *Transplant Proc.* 23:1083–1806 (1991).
Mattar et al., "Inhibition of the epidermal growth factor receptor tyrosine kinase activity by leflunomide," *FEBS Letters* 2:161–164 (1993).
McChesney et al., "An Evaluation of Leflunomide in the Canine Renal Transplantation Model," *Transplantation* 57:1717–1722 (1994).
Nichterlein et al., "Leflunomide (HWA 486) Prolongs Course of Murine Listeriosis," *Immunol. Infect. Dis.* 4:18–22 (1994).
Ogawa et al., "Effects of leflunomide on glomerulonephritis induced by antibasement membrane antibody in rats," *Agents Actions* 31:321–328 (1990).
Ogawa et al., "Therapeutic Effects of Leflunomide, a New Antirheumatic Drug, on Glomerulonephritis Induced by the Antibasement Membrane Antibody in Rats," *Clin. Immunol. Immunopath.* 61:103–118 (1991).
Ross, "The pathogenesis of atherosclerosis: a perspective for the 1990s," *Nature* 362:801–809 (1993).
Schorlemmer et al., "Prolongation of Allogeneic Transplanted Skin Grafts and Induction of Tolerance by Leflunomide, a New Immunosuppresive Isoxazol Derivative,"0 *Transplant. Proc.* 25:763–767 (1993).

(List continued on next page.)

*Primary Examiner*—Phyllis G. Spivack
*Attorney, Agent, or Firm*—Lyon & Lyon

[57] ABSTRACT

Pharmaceutical formulations containing a lipophilic compound solubilized in ethanol and a surfactant are disclosed. The solubilized compound can then be further dissolved in a pharmaceutically acceptable aqueous solution to form a pharmaceutical formulation suitable for patient administration. Preferred lipophilic compounds are 5-methylisoxazole-4-carboxylic acid-(4-trifluoromethyl)-auilide and N-(4-triflouromethylphenyl)-2-cyano-3-hydroxycrotonamide.

18 Claims, No Drawings

OTHER PUBLICATIONS

Thoenes et al., "Leflunomide (HWA 486) Inhibits Experimental Autoimmune Tubulointerstitial Nephritis in Rats," *Int. J. Immunopharmacol.* 11:921–929 (1989).

Ulrichs et al., "Suppression of Natural Xenophile Antibodies With the Novel Immunomodulating Drug Leflunomide," *Transplant Proc.* 24:718–719 (1992).

Weithmann et al., "Effect of leflunomide on constitutive and inducible pathways of cellular eicosanoid generation," *Agents Actions* 41:164–170 (1994).

Williams et al., "Immunosuppressive Effects of Leflunomide in a Cardiac Allograft Model," *Transplantaion Proc.* 25:745–746 (1993).

Williams et al., "Leflunomide in Experimental Transplantation," *Transplantation* 57:1223–1231 (1994).

Xiao et al., "Leflunomide Controls Rejection in Hamster to Rat Cardiac Xenografts," *Transplantaiton* 58:828–834 (1994).

Xiao et al., "Effect of Leflunomide in Control of Acute Rejection in Hamster–to–Rat Cardiac Xenografts," *Transplantation Proceedings* 26:1263–1265 (1994).

Zeilinski et al., "Effects of leflunomide (HWA 486) on expression of lymphocyte activation markers," *Agents Actions* 38:(Special Conference Issue) C80–C82 (1993).

Bristol Laboratories Oncology Products, "VePesid (Etoposide) For Injection and Capsules," Dec. 1992.

FORMULATIONS FOR LIPOPHILIC COMPOUNDS

PRIOR APPLICATIONS

The present application is a Continuation-In-Part of Hirth et al., entitled "TREATMENT OF PLATELET DERIVED GROWTH FACTOR RELATED DISORDERS SUCH AS CANCERS" U.S. Ser. No. 08/370,574, filed Jan. 6, 1995, which is a Continuation-In-Part of Hirth et al. U.S. Ser. No. 08/179,570, filed Jan. 7, 1994.

FIELD OF THE INVENTION

The present invention features pharmaceutical formulations containing lipophilic compounds.

BACKGROUND OF THE INVENTION

Various methods are available for administering therapeutic agents into a patient. Such methods include, parenteral, oral, ocular, nasal, topical, and transmucosal administration. Variations of these different types of administrations exist. For example, parenteral administration includes intravenous, subcutaneous, intraperitoneal, intramuscular, and intramedullary injection. The chosen mode of administration should take into account the nature of the therapeutic compound and the illness being treated.

Lipophilic compounds are non-polar and have low solubility in water. Different techniques concerned with solubilizing lipophilic compounds include those described by Praveen et al., U.S. Pat. No. 5,314,685, and Fernandes et al., U.S. Pat. No. 4,992,271.

SUMMARY OF THE INVENTION

The present invention features pharmaceutical formulations containing a lipophilic compound. The lipophilic compound is solubilized in solution containing alcohol (i.e. ethanol) and a surfactant. The solubilized compound can then be further dissolved in a pharmaceutically acceptable aqueous solution, such as WFI (water for injection), D5W (5% dextrose in water), and D5W 0.45% saline, to form a pharmaceutical formulation suitable for patient administration. The formulation is preferably used for parenteral administration.

Thus, a first aspect of the present invention features a formulation containing the following: (a) a solution made up of a pharmaceutically acceptable surfactant and alcohol in a ratio of 10:1 to 1:10 (v/v); and (b) preferably at least 1 mg/ml of a lipophilic compound. The compound is soluble in the formulation.

In preferred embodiments concerning the ratio, the ratio is preferably 10:1 to 1:2 (v/v), more preferably 2:1 to 1:2 (v/v).

In preferred embodiments concerning the amount of lipophilic compound, the amount is preferably 5 mg/ml, more preferably 10 mg/ml.

A "lipophilic compound" refers to a non-polar compound having a greater solubility in aqueous solution than in non-polar organic solvents such as long chain alcohols. The formulations described by the present invention facilitate solubilization of lipophilic compounds which readily dissolve in alcohol. Preferably, the lipophilic compound is insoluble in aqueous solution. More preferably, the compound has the solubility characteristics in alcohol and aqueous solution as 5-methylisoxazole-4 carboxylic acid-(4-trifluromethyl)-anilide (also known as leflunomide).

The surfactant is added to allow for dilution into a pharmaceutically acceptable solution prior to patient administration. Preferably, the surfactant is a non-ionic surfactant. Examples of pharmaceutically acceptable surfactants include POLYSORBATE 80® and other polyoxyethylene sorbitan fatty acid esters, glyceryl monooleate, polyvinyl alcohol, and sorbitan esters.

The solution containing the lipophilic compound is preferably adjusted to a pH where the lipophilic compound is stable. In a preferred embodiment, the pH is adjusted to between 2 and 7. The pH can be adjusted using pharmaceutically acceptable excipients such as ascorbic acid, citric acid, lactic acid, acetic acid, tartaric acid, sodium sulfate, hydrochloric acid, sodium hydroxide, glycerine, sodium phosphate and sodium acetate.

Because of the alcohol content, the formulation should be dissolved in a sufficient amount of a pharmaceutically acceptable aqueous solution prior to patient administration to avoid toxic effects due to the alcohol content. The added amount of a pharmaceutically acceptable aqueous solution should be sufficient to avoid hemolysis. Preferably, the alcohol:surfactant solution is diluted at least 1:5 (v/v), more preferably at least 1:10 (v/v), and most preferably 1:15 (v/v) with aqueous solution to provide a pharmaceutically acceptable formulation. Examples of suitable pharmaceutically acceptable aqueous solutions such as WFI and solutions containing isotonic saline are known in the art.

By "pharmaceutically acceptable" or "pharmaceutical" in reference to the different formulation components, or the formulation itself, means that components or formulation do not prevent the therapeutic compound from exerting a therapeutic effect and do not cause unacceptable adverse side effects. Examples of pharmaceutically acceptable reagents are provided in *The United States Pharmacopeia The National Formulary*, United States Pharmacopeial Convention, Inc., Rockville, Md. 1990 (hereby incorporated by reference herein into the present application), Unacceptable side effects vary for different diseases. Generally, the more severe the disease the more toxic effects which will be tolerated. Unacceptable side effects for different diseases are known in the art.

A second aspect of the present invention features the use of the formulations described above to treat patients. The formulations can be used to treat different disorders preferably hyper-proliferative cell disorders. Preferably, the therapeutic agent is administered parenterally.

"Hyper-proliferative cell disorders" refer to disorders where an excess cell proliferation of one or more subset of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the effected cells. Hyper-proliferative cell disorders include cancers, blood vessel proliferative disorders, fibrotic disorders, and autoimmune disorders.

Other features and advantages of the invention will be apparent from the following description of the preferred embodiments thereof, and from the claims.

DETAILED DESCRIPTION OF THE INVENTION

The present invention features a formulation containing alcohol and a surfactant for solubilizing lipophilic therapeutic agents. The formulation can be used to facilitate administration of lipophilic compounds to a patient in need of such treatment.

The ability to prepare a lipophilic compound for therapeutic administration is illustrated below by reference to leflunomide. Based on the guidelines provided below and the known therapeutical utility of other lipophilic compounds, the present invention can be used to prepare formulations with these other compounds to facilitate treatment of patients, preferably human patients.

I. Lipophilic Compounds

The present invention can be used to formulate different lipophilic compounds for therapeutic administration. For example, compounds structurally related to leflunomide and N-(4-trifluoro-methylphenyl)-2-cyano-3-hydroxycrotonamide, such as those reference in Section I.B. infra., which are soluble in alcohol and have little or none aqueous solubility can be formulated for therapeutic administration using the present invention.

Additional lipophilic compounds can be identified based on their known physical characteristics and therapeutic applications. For example, compounds listed in Physician Desk Reference (Edition 48, 1994) which are indicated to be insoluble in aqueous solution or soluble in POLYSORBATE 80® are good candidate compounds. Examples of such compounds include Taxol, etoposide, BCNU, medroxyprogesterone, teniposide, and dexamethasone. Another source of candidate compounds are those compounds described by Cho Tang entitled "Compounds and Methods for Inhibiting Hyper-Proliferative Cell Growth," U.S. application Ser. No. 08/426,789, filed Apr. 21, 1995, which is hereby incorporated by reference herein. The ability of such compounds to be dissolved in alcohol and preparation of a particular pharmaceutical formulation can be carried out using the guidelines described herein which are illustrated by the preparation of leflunomide formulations.

A. Leflunomide Formulations

Leflunomide has a low solubility in standard formulations used to dissolve compounds for parenteral administration. For example, the solubility of leflunomide in VPD (126 mg alcohol, 40 mg POLYSORBATE 80®, 3 mg citric acid, 15 mg benzyl alcohol, and 325 mg PEG MW300; also referred to as PBTE) is about 60 mg/ml. Parenterally administered VPD formulations should be diluted at least 1:2 with a pharmaceutically acceptable aqueous solution to avoid toxic effects. Such dilution can result in precipitation of lipophilic compounds. For leflunomide, a concentration in VPD greater than about 5 mg/ml precipitates when diluted 1:2 with a pharmaceutically aqueous solution such as WFI.

Increasing the solubility of leflunomide allows more leflunomide to be administered to a patient via parenteral administration. The formulations described by the present invention can use alcohol and a surfactant to solubilize leflunomide. Leflunomide is soluble in alcohol at 100 mg/ml. The surfactant is added to allow for the dilution into a pharmaceutically acceptable aqueous solution prior to injection.

The stability of leflunomide in solution is pH dependent, basic pH leads to the breakdown to N-(4-trifluoro-methylphenyl)-2-cyano-3-hydroxycrotonamide. The pH of the formulations can be adjusted with a pharmaceutically acceptable excipient. For example, the apparent pH of the POLYSORBATE 80®: alcohol formulations can be adjusted with citric acid.

Leflunomide is preferably adjusted to a pH of between 4 and 6 using a physiologically acceptable excipient. A further decrease in pH will occur upon dilution with aqueous solution. For example, a 1:1 or greater dilution with aqueous solution will result in a pH of 2.5 to 4.0.

As noted above, the alcohol:surfactant formulation should not be directly used in a patient because of the high alcohol content and a sufficient amount of pharmaceutically acceptable aqueous should be used to avoid toxic alcohol effects. Preferably, the alcohol solution is diluted at least 1:5, more preferably the solution is diluted at least 1:10, most preferably at least 1:15, to provide a pharmaceutically acceptable formulation.

Increasing 5-methylisoxazole-4 carboxylic acid-(4-trifluromethyl)-anilide solubility offers several advantages. For example, a larger amount of 5-methylisoxazole-4 carboxylic acid-(4-trifluromethyl)-anilide can be added at one time to achieve a longer effect thereby decreasing the need for continuous dosing, a higher concentration allows more drug to be delivered in less total volume, a larger amount of drug may be needed to achieve a certain therapeutic effectiveness, and the increase in solubility reduces the need for formulations which can have adverse side effects.

B. Leflunomide and Related Compounds Leflunomide, N-(4-trifluoro-methylphenyl)-2-cyano-3hydroxycrotonamide, and structurally related compounds have been said to be useful in inhibiting hyper-proliferative cell growth. Leflunomide acts as a prodrug for the in vivo formation of N-(4-trifluoro-methylphenyl)-2-cyano-3-hydroxycrotonamide, which appears to the active drug. According to the abstracts of Kömmerer F-J, et al., U.S. Pat. No. 4,284,786 (1981) and Kömmerer F-J, et al., U.S. Pat. No. 4,351,841 (1982) (each of these references are hereby incorporated by reference herein), leflunomide:

> . . . has antirheumatic, antiphlogistic, antipyretic and analgesic action, and can be used for the treatment of multiple sclerosis.

Heubach, U.S. Pat. No. 4,087,535 (1978) (hereby incorporated by reference herein) indicates that leflunomide has anti-inflammatory and analgetic properties. Robertson S. M. and Lang L. S., European Patent Application 0 413 329 A2 (published 1991) which is concerned with 5-methylisoxazole-4-carboxylic acids that encompass leflunomide (hereby incorporated by reference herein), assert:

> The present invention is directed to methods for treating ocular diseases with immune etiology through the use of 5-methyl-isoxazole-4-carboxylic acid anilides and hydroxyethlidene-cyano acetic acid anilide derivatives. In addition the compounds are useful for treating ocular manifestation associated with systemic diseases with immune etiology. The compounds exhibit immunosuppressive, antiinflammatory, and mild antiallergic activity and are useful for the treatment of eye diseases such as uveitis (including rheumatoid nodules), retinitis, allergy (vernal keratocon junctivitis and allergic or giant papillar conjunctivitis) and dry eye (Sjogren's syndrome). Additionally the compounds are useful for prolonging graft survival of corneal or other ocular tissue and are useful as surgical adjuncts in patients which are atopic or immune impaired.

The abstract of Bartlett R. R. et al., entitled "Isoxazole-4-Carboxamides and Hydroxyalklidene-Cyanoacetamides, Drugs Containing These Compounds and Use of Such Drugs" PCT/EP90/01800 (hereby incorporated by reference herein), asserts:

> Isoxazole-4-carboxamide derivatives and hydroxy-alkylidene-cyanoacetamide derivatives are suitable for the treatment of cancer diseases. These compounds can be prepared by prior art methods. Some of them are new and are suitable, in addition, for the treatment of rheumatic diseases.

Bartlett et al., U.S. Pat. No. 5,268,382 (1993) (hereby incorporated by reference herein), mentions the use of leflunomide and N-(4-trifluoro-methylphenyl)-2-cyano-3-hydroxycrotonamide to combat chronic graft-versu-shost diseases, and in particular systemic lupus erythematosus.

Bartlett R. R. et al., *Agents and Actions* 32:10–21 (1991) (hereby incorporated by reference herein), indicates leflunomide was shown to be very effective in preventing and curing several autoimmune animal diseases.

Other publications concerning leflunomide, N-(4-trifluoro-methylphenyl)-2-cyano-3-hydroxycrotonamide, and structurally related compounds include the following; Bartlett et al., *Leflunomide: A novel immunomodulating drug in: Nonsteroidal Anti-Inflammatory Drugs* (2nd ed.) pp. 349–366, Eds. Lewis and Furst, Dekker, N.Y. N.Y.; *Pharmaprojects*, PJB Publications Lts, Richmond, Surrey, U. K.; *Hoechst Present Future Plans, in: R & D Focus Drug News*, Oct. 3, 1994; *Hoechst Licensing and R & D update, in: R & D Focus Drug News*, Feb. 10, 1992; *Leflunomide, in: R & D Focus Drug News*, May 23, 1994; Xiao et al., *Transplantation* 58:828–834, 1994; Xiao et al., *Transplantation* 26:1263–1265, 1994; McChesney, et al., *Transplantation*, 57:1717–1722, 1994; Bartlett, et al., *Springer Semin. Immunopathol.*, 14:381–394, 1993; Nichterlein, et al., *Immunol. Infect. Dis.* 4:18–22, 1994; Williams, et al., *Transplantation*, 57:1223–1231, 1994; Weithmann, et al., entitled "*Use of Leflunomide for the Inhibition of Interleukin 1.alpha,*" EP 6077742 A2, 940727; Weithmann, et al., entitled "*Use of Leflunomide for the Inhibition of Interleukin 1.beta,*" EP 607775 A2, 940727; Weithmann, et al., entitled "*Use of Leflunomide for the Inhibition of Tumor Necrosis Factor .alpha.* (TNF-.alpha.) EP 607776 A2, 940727; Weithmann, et al., entitled "*Use of Leflunomide for the Inhibition of Interleukin 8*", EP 607777 A2, 940727; Ju, et al., *Yaoxue Xuebao*, 92:90–94, 1994; Weithmann, et al., *Agents Actions*, 41:164–170, 1994; Ju, et al., *Zhongguo Yaoli Xuebao*, 15: 223–226, 1994; Chong, et al., *Transplantation*, 55:1361–1366, 1993; Zielinski, et al., *Agents Actions*, 38: (Special Conference Issue) C80–C82, 1993; Chong, et al., *Transplant. Proc.*, 25:747–749, 1993; Williams, et al., *Transplant. Proc.*, 25:745–746, 1993; Schorlemmer, et al., *Transplant. Proc.*, 25:763–767, 1993; Glant, et al., *Immunopharmacology*, 23:105–116, 1992; Ulrichs, et al, *Transplant. Proc.*, 24:718–719, 1992; Ogawa, e t al, *Clin. Immunol. Immunopathol.*, 61: 103–118, 1991; Kuechle, et al., *Transplant. Proc.*, 23:1083–1086, 1991; Ogawa, et al, *Agents Actions*, 31:321–328, 1990; and Thoenes, et al., *Int. J. Immunopharmacol.*, 11:921–929, 1989; and Bartlett et al., entitled "Derivès 2-cyano 3-hydroxy enamides, leur proc èdè depreparation, leur application comme medicaments, les compositions pharmaceutiques les renfermant et les interm èdiaires obtenus" 0 551 230 A1. (Each of these references are hereby incorporated by reference herein into the present application.)

Leflunomide, N-(4-trifluoro-methylphenyl)-2-cyano-3-hydroxycrotonamide and related compounds can be also used to treat various hyper-proliferative cell disorders as described by Hirth et al., entitled "Treatment of Platelet Derived Growth Factor Related Disorders Such as Cancers" U.S. Ser. No. 08/370,574. (SUGEN Inc., the assignee of the present invention is a joint assignee of U.S. Ser. No. 08/370, 574 which is hereby incorporated by reference herein into the present application).

II. Hyper-Proliferative Cell Disorders

Hyper-proliferative cell disorders include cancers, blood vessel proliferation disorders, fibrotic disorders and autoimmune disorder. These disorders are not necessarily independent. For example, fibrotic disorders may be related to, or overlap with, blood vessel disorders. For example, atherosclerosis (which is characterized herein as a blood vessel disorder) results in the abnormal formation of fibrous tissue.

Blood vessel proliferation disorders refer to angiogenic and vasculogenic disorders generally resulting in abnormal proliferation of blood vessels. Examples of such disorders include restenosis, retinopathies, and atherosclerosis. The advanced lesions of atherosclerosis result from an excessive inflammatory-proliferative response to an insult to the endothelium and smooth muscle of the artery wall. (Ross R., *Nature* 362:801–809 (1993).) Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorders are due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial disorders are brought about by abnormal proliferation of mesangial cells. Mesangial hyper-proliferative cell disorders include various human renal diseases, such as glomerulonephritis, diabetic nephropathy, malignant nephrosclerosis, thrombotic microangiopathy syndromes, transplant rejection, and glomerulopathies.

Cancers can be caused by abnormal growth of different types of cells. A "cancer cell" refers to various types of malignant neoplasms, most of which can invade surrounding tissues and may metastasize to different sites, as defined by Stedman's Medical Dictionary 25th edition (Hensyl ed. 1990). Examples of cancers which may be treated by formulations such as leflunomide include intra-axial brain cancers, ovarian cancers, colon cancers, prostate cancers, lung cancers, Kaposi's sarcoma and skin cancers.

These different types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development by facilitating vascularization of solid cancers. Thus, cancer growth can be inhibited through different mechanisms such as directly inhibiting the growth of cancer cells and/or inhibiting the growth of cells supporting cancer growth.

A. Ovarian Cancer

Epithelial ovarian cancer accounts for nearly 90% of all ovarian tumors and continues to be a highly lethal malignancy. Treatment for advanced ovarian cancer generally includes cytoreductive surgery followed by combination chemotherapy with alkylating agents such as cisplatin and cyclophosphamide. However, long term survival of advanced ovarian cancer patients is extremely poor, in the range of 10%–20%, principally because of the high incidence of metastatic tumors throughout the peritoneal cavity, and, in some cases, the lymph-nodes. Moreover, chemotherapy with cisplatin carries a potential for renal toxicity and progressive neuropathy.

Treatment of ovarian cancers can be carried out by administering leflunomide to supporting stromal cells (i.e., the framework upon which a tumor or metastatic lesion grows, including but not limited to connective tissue and vascular endothelial cells), and/or in associated vascular endothelial cells. In view of the localized spread of ovarian cancer throughout the peritoneal cavity, a preferred method of administration, particularly in advanced cases, is by intravenous or intraperitoneal injection.

B. Glioma

The compounds described herein can also be used in the treatment of primary intra-axial brain tumors of the glioma family, such as astrocytomas and glioblastomas. Glioblastoma multiforme is the most common and most malignant tumor of astrocytic origin in human adults and accounts for more than half of all primary brain tumors (See, for example, *Cecil Textbook of Medicine*, Wyngaarden, Smith, Bennett (eds) WB Saunders, 1992, p. 2220).

Intravenous and intra-arterial routes are considered to be preferred routes of administration. In addition, micro-catheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

III. Dosage

The proper dosage depends on various factors such as the type of disease being treated, the particular composition being used, and the size and physiological condition of the patient. Therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

A "therapeutically effective amount," in reference to the treatment of a cancer refers to an amount sufficient to bring about one or more or the following results: reduce the size of the cancer; inhibit the metastasis of the cancer; inhibit the growth of the cancer, preferably stop cancer growth; relieve discomfort due to the cancer; and prolong the life of a patient inflicted with the cancer.

A "therapeutically effective amount," in reference to the treatment of a hyper-proliferative cell disorder other than a cancer refers to an amount sufficient to bring about one or more of the following results: inhibit the growth of cells causing the disorder, preferably stopping the cell growth; relieve discomfort due to the disorder; and prolong the life of a patient suffering from the disorder.

Plasma half-life and biodistribution of the drug and metabolites in the plasma, tumors, and major organs can be also be determined to facilitate the selection of drugs most appropriate to inhibit a disorder. Such measurements can be carried out, for example, HPLC analysis can be performed on the plasma of animals treated with the drug and the location of radiolabeled compounds can be determined using detection methods such as X-ray, CAT scan, and MRI. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out as follows: 1) the compound is administered to mice (an untreated control mouse should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each toxicity study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose leflunomide is between 1 to 500 mg/day, preferably 1 to 250 mg/day, and most preferably 1 to 50 mg/day. Drugs can be delivered less frequently provided plasma levels of the active moiety are sufficient to maintain therapeutic effectiveness.

Plasma levels should reflect the potency of the drug. Generally, the more potent the compound the lower the plasma levels necessary to achieve efficacy.

IV. Example

The example provided below illustrates different aspects and embodiments of the present invention. The example is not intended to limit the invention.

Leflunomide was solubilized in varying ratios of POLYSORBATE 80® and alcohol. The leflunomide solutions were then tested for the ability to dilute with aqueous solutions. The results are shown in Table I.

TABLE I

| Vehicle* | Concentration | Solubility | Maximum dilution of vehicle with 0.9% NaCl** |
|---|---|---|---|
| PBTE6C:WFI | 2.5 mg/ml | Soluble | 1:7.5 |
| alcohol | 100 mg/ml | Soluble | |
| 33% T:66% E | 100 mg/ml | Insoluble | |
| | 50 mg/ml | Soluble | 1:1 |
| | 25 mg/ml | Soluble | ≧1:30 |
| 50% T:50% E | 100 mg/ml | Soluble | 1:1 |
| | 75 mg/ml | Soluble | 1:1 |
| | 60 mg/ml | Soluble | 1:1 |
| | 55 mg/ml | Soluble | 1:1 |
| | 50 mg/ml | Soluble | 1:1 |
| 66% T:33% E | 100 mg/ml | Insoluble | |
| | 50 mg/ml | Soluble | ≧1:100 |

PBTE6C:WFI refers to 3% benzyl alcohol; 80% POLYSORBATE 80 ®; 65% PEG MW 300; 24% alcohol; and 6 mg/ml citric acid.
*33% T:66% E (33% POLYSORBATE 80 ® and 66% parts alcohol, v/v); 50% T:50% E (50% POLYSORBATE 80 ® and 50% alcohol, v/v); 66% T:33% E (66% POLYSORBATE ® 80 to 33% alcohol, v/v).
**The same results were obtained using dilutions with 0.45% NaCl, WFI, 5% dextrose in water, and a solution containing 0.45% NaCl and 5% dextrose in water.

Table I demonstrates that POLYSORBATE 80®:alcohol (33%:66% v/v) or (66%:33%, v/v) works well in the solubilization process (designated 33%T:66%E and 66%E:33%T, respectively). These formulations allow increased solubility of leflunomide and dilution with aqueous solutions (25 mg/ml in 33%T:66%E or 50 mg/ml in 66%T:33%E).

As noted above, the stability of leflunomide in solution is pH dependent. To stabilize leflunomide varying amounts of citric acid (1 to 20 mg/ml) were added to both 33%T:66%E and 66%T:33%E. The citric acid decreased the apparent pH of the solutions. However, leflunomide was no longer soluble to the same extent in 33%:66%E. Thus, a ratio of surfactant to alcohol of about (i.e.±50% for each component) 1:2 is preferred.

The pH of 33%T:66%E and 4 mg/ml citric acid) is 5.3 and the pH of 33%T:66%E and 6 mg/ml citric acid) is 5.2. Upon dilution of these vehicles with 0.45% NaCl, WFI, 0.9% NaCl, or a solution containing 0.45% NaCl and 5% dextrose in water, the pH decreased to ~3.

With time leflunomide at 25 mg/ml in 33%T:66%E falls out of solution (precipitation) at room temperature (22° C. to 26° C.) when diluted with aqueous solutions over 3 days. Leflunomide at 20 mg/ml remains in solution in 33%T:66%E (with either 4 or 6 mg/ml citric acid) at both room temperature and 4° C. At 2°–8° C. for 7 days, precipitate started to occur.

Other embodiments are within the following claims. Thus, while several embodiments have been shown and described, various modifications may be made, without departing from the spirit and scope of the present invention.

We claim:

1. A formulation comprising:
   a) a first solution comprising a pharmaceutically acceptable surfactant and ethanol in a surfactant:ethanol ratio of 10:1 to 1:10 (v/v), and
   b) at least 1 mg/ml of a lipophilic compound, wherein said lipophilic compound comprises either an isoxazole group or a cyanoacetamide group.

2. The formulation of claim 1, wherein said first solution further comprises a pharmaceutically acceptable excipient to provide a pH of 2 to 7, and said compound is either 5-methyl-isoxazole-4 carboxylic acid-(4-trifluoromethyl)-anilide or N-(4-trifluoro-methylphenyl)-2-cyano-3-hydroxycrotonamide.

3. The formulation of claim 2, where said first solution is diluted at least 1:5 in a pharmaceutically acceptable aqueous solution to form a pharmaceutically acceptable formulation.

4. The formulation of claim 3, where said first solution is diluted at least 1:10 in said pharmaceutically acceptable aqueous solution to form said pharmaceutically acceptable formulation.

5. The formulation of claim 4, wherein said surfactant:ethanol ratio is 10:1 to 1:2 (v/v).

6. The formulation of claim 5, wherein said pharmaceutical surfactant is POLYSORBATE 80®.

7. The formulation of claim 4, wherein said compound is 5-methylisoxazole-4 carboxylic acid-(4-trifluoromethyl)-anilide.

8. The formulation of claim 4, wherein said compound is N-(4-trifluoro-methylphenyl)-2-cyano-3-hydroxycrotonamide.

9. The formulation of claim 4, wherein said surfactant:ethanol ratio is about 1:2.

10. The formulation of claim 1, wherein at least 5 mg/ml of said compound are present, and said compound is either 5-methylisoxazole-4 carboxylic acid-(4-trifluoromethyl)-anilide or N-(4-trifluoro-methylphenyl)-2-cyano-3-hydroxycrotonamide.

11. A method of treating a patient using a lipophilic compound comprising the steps of:
   a) diluting a formulation with a pharmaceutically acceptable aqueous solution to form a pharmaceutically acceptable formulation, said formulation comprising:
      a first solution comprising a pharmaceutical surfactant and alcohol in a surfactant:ethanol ratio of 10:1 to 1:10 (v/v) and at least 1 mg/ml of said lipophilic compound, wherein said lipophilic compound comprises either an isoxazole group or a cyanoacetamide group; and
   b) administering said pharmaceutical formulation to said patient.

12. The method of claim 11, wherein said pharmaceutical formulation further comprises a physiological excipient to provide a pH of 2 to 7.

13. The method of claim 12, where said formulation is diluted at least 1:10 with a pharmaceutically acceptable aqueous solution to form said pharmaceutical formulation.

14. The method of claim 13, wherein said patient has a hyperproliferative cell disorder and said lipophilic compound is either 5-methylisoxazole-4 carboxylic acid-(4-trifluoromethyl)-anilide or N-(4-trifluoro-methylphenyl)-2-cyano-3-hydroxycrotonamide.

15. The method of claim 14, wherein said surfactant:ethanol ratio is 10:1 to 1:2.

16. The method of claim 15, wherein said surfactant:ethanol ratio is about 1:2.

17. The method of claim 15, wherein said compound is 5-methylisoxazole-4 carboxylic acid-(4-trifluoromethyl)-anilide.

18. The method of claim 15, wherein said compound is N-(4-trifluoro-methylphenyl)-2-cyano-3-hydroxycrotonamide.

* * * * *